United States Patent [19]
Mackin et al.

[11] Patent Number: 4,809,677
[45] Date of Patent: Mar. 7, 1989

[54] HEATER TRAVERSE MECHANISM FOR INFANT CARE CENTER

[75] Inventors: Michael H. Mackin, Columbia; Robert J. Koch, Ellicott City, both of Md.

[73] Assignee: The BOC Group, Inc., Montvale, N.J.

[21] Appl. No.: 96,565

[22] Filed: Sep. 14, 1987

[51] Int. Cl.$^4$ .............................. A61F 7/00; F24H 9/06
[52] U.S. Cl. ...................................... 600/22; 128/399; 219/348
[58] Field of Search .......... 128/1 B, 399, 362, 205.26; 219/345 X, 347 X, 348 X, 354 X

[56] References Cited

U.S. PATENT DOCUMENTS

| | | | |
|---|---|---|---|
| 3,858,570 | 1/1975 | Beld et al. | 128/1 B |
| 4,161,172 | 7/1979 | Pickering | 128/1 B |
| 4,658,828 | 4/1987 | Dory | 128/399 |

FOREIGN PATENT DOCUMENTS 508667  2/1952  Belgium .............................. 128/1 B Primary Examiner—William L. Freeh
Attorney, Agent, or Firm—Larry R. Cassett; Roger M. Rathbun

[57] ABSTRACT

A heater traverse mechanism used with an infant care center is disclosed. The traverse mechanism allows the heater that is focused on or about the infant positioned on the infant care center to be moved aside for better access to the infant, yet, as the heater is moved, the traverse mechanism automatically adjusts the heater such that its focus remains on the infant so that even at various points along a locus, the footprint of heat on or about the infant remains relatively constant.

9 Claims, 5 Drawing Sheets

HEATER TRAVERSE MECHANISM FOR INFANT CARE CENTER

BACKGROUND OF THE INVENTION

The present invention relates to infant care centers of the type that provide a support or bed for the infant and which provide care facilities for that infant.

In particularly, the invention relates to such infant care centers that include overhead heating units that direct heat to the infant when that infant is positioned upon the infant bed.

Typically, such heaters focus the effect of heat emitted therefrom to a relatively narrow focus on or about the infant positioned on the infant bed in order to optimize the heat to the infant to the extent possible.

Also, in a typical infant care center, the heater is mounted such that it can be manually moved by attending personnel out of the way of such attending personnel in the event greater access is desired to the infant, such as when X-rays are being taken.

At such times, however, when the heater is moved from its preset focused position, the focus is disrupted and no longer is directed on or about the infant; thus the optimum heat is not, at such times, being delivered to the infant.

SUMMARY OF THE INVENTION

The infant care center of the present invention has generally a freestanding frame from which is suspended an infant bed. Above the infant bed is mounted a heater that is focused such that its heat is directed on or about an infant positioned upon the infant bed. The heater is movable by attending personnel to various positions out of the normal position to attain greater access to the infant. A mounting mechanism is employed such that when the heater is moved to different locations along a locus, the heater continues to direct the heat toward the infant such that the heat remains focused on or about the infant throughout the movement of the heater. In the preferred embodiment, the heater is moved laterally across the infant bed in a plane generally parallel to the plane of the infant bed and the heater is rotated as it moves to maintain the desired focus. As an alternate embodiment, the heater does not rotate about its mounting but travels in a predetermined arcuate locus across the infant bed with the center point of the radius for that arc remaining at or near the infant positioned upon the infant bed.

Thus, with either embodiment, attending personnel can easily move the heater out of its normal position to various remote positions to gain more complete access to the infant, yet the optimum heat to the infant is not sacrificed by altering to any large extent, the focus of the heat from the heater directed on or about the infant.

DESCRIPTION OF THE PREFERRED EMBODIMENT

Figure 1:
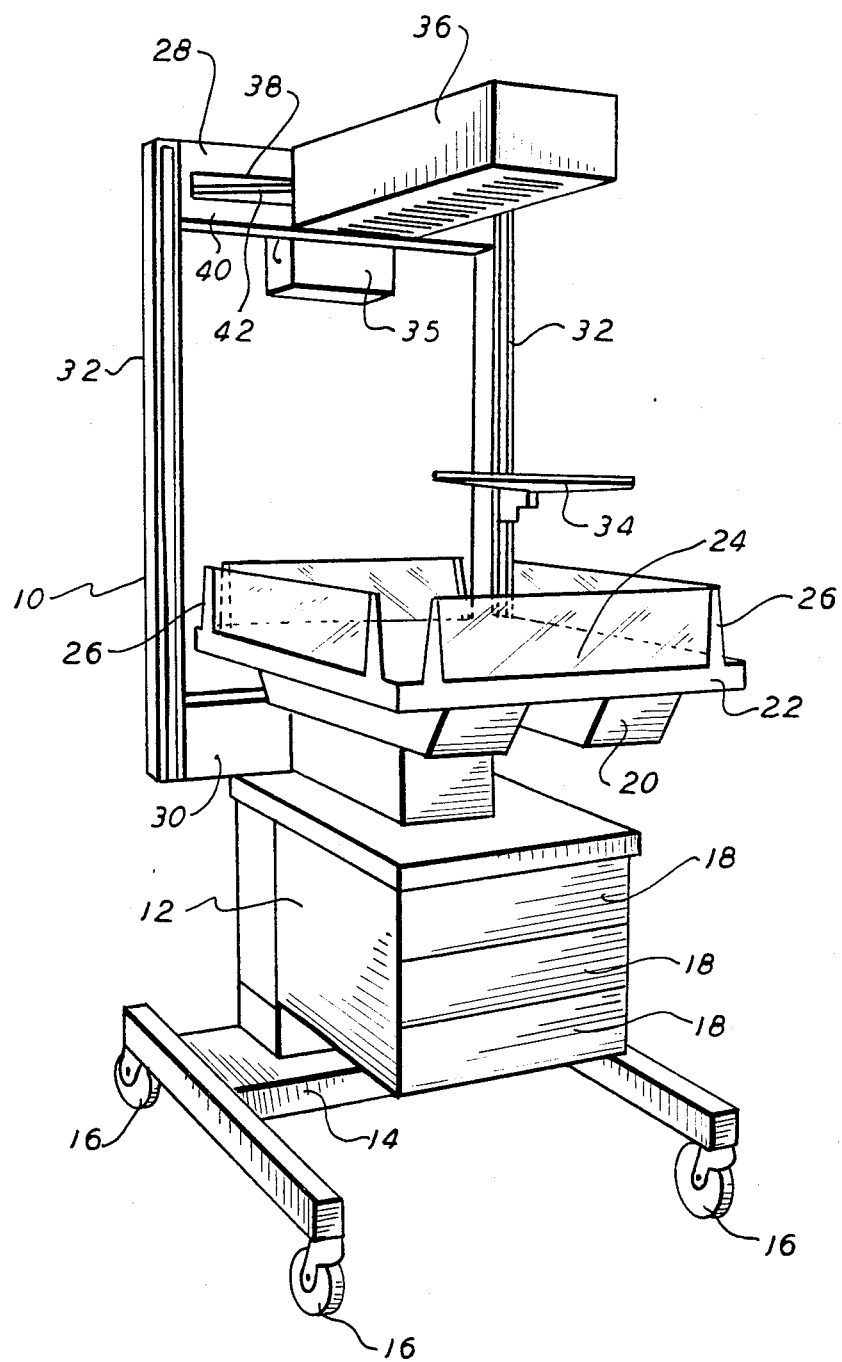
FIG. 1 is an isometric view of an infant care center having the heater traverse mechanism of the present invention.

Referring now to FIG. 1, there is shown an isometric view of an infant care center having a heater traverse mechanism constructed in accordance with the present invention. As shown, the care center includes a frame 10 which provides a free standing unit for the care center. The frame 10 is supported upon a cabinet 12 which, in turn, is mounted upon a base 14 having wheels 16 so that the care center is easily movable. The cabinet 12 may also include one or more drawers 18 for containing items for attending to an infant.

An infant pedestal 20 is mounted atop of the cabinet 12 and on which is located an infant bed 22 which underlies an infant positioned thereon. Pedestal 20 is the main support for infant bed 22. The infant bed 22 has a generally planar upper surface 24 with appropriate cushioning material for comfort of the infant and further may be surrounded by guards 26, generally of a clear plastic material, and which contain the infant on the upper surface 24. Generally, the guards 26 are releasable and/or removable for complete access to the infant.

Frame 10 includes upper and lower cross members, 28 and 30, respectively, joining a pair of vertical struts 32 and which vertical struts 32 may provide a means of support for other structural parts such as a shelf 34.

Mounted on the upper cross member 28 may be a control module 35 for containing the various electrical controls to operate the care center. In addition, in accordance with the preferred embodiment, a heater 36 is mounted to the upper cross member 28 in a manner to be later described. As will be noted, the location of heater 36 is such as to be above the infant bed 22 so that radiant heat is directed from heater 36 downwardly to warm an infant positioned upon the planar upper surface 24 of infant bed 22. That heater 36 is focused so as to provide a footprint on or around the infant to optimize the amount of heat directed upon the infant. Various types of focusable heaters are available for such application, examples of which may be a Calrod focused heater of about 500–600 watts, or a corrugated foil heater. Preferably, the heater is of a linear length such that the footprint of heat is generally rectangular.

An elongated opening 38 is formed in the front cover 40 of the upper cross member 28 as will be later explained and, within elongated opening 38 may be seen in FIG. 1, a portion of an inclined track 42.

Figure 2:
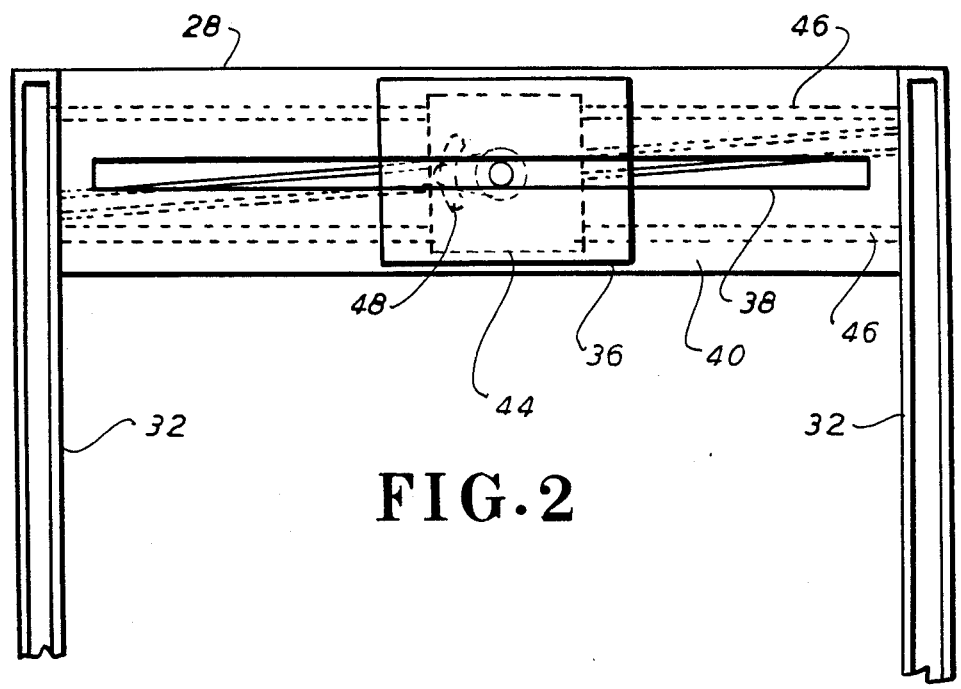
FIG. 2 is an enlarged front view, partly broken away, of the preferred embodiment of the mounting means for the heater of the present invention.

Turning now to FIG. 2, there is shown an enlarged front view, partly broken away, of the infant care center and specifically showing the heater 36 for directing radiant heat toward the infant. As may also be seen in FIG. 2, the upper cross member 28 has, in its front cover 40 the elongated opening 38 that extends substantially along the entire length of upper cross member 28.

A carriage 44 is located within the upper cross member 28 and is movable substantially along the length of upper cross member 28 by being supported on a pair of rods 46 that span the length of the upper cross member 28 and may be held in position within upper cross member 28 by conventional means. In the preferred embodiment of FIG. 2, the rods 46 are generally horizontal and are essentially parallel to the planar upper surface 24 of infant bed 22. An opening 48 is formed in carriage 44, again, which will be later explained.

Figure 3:
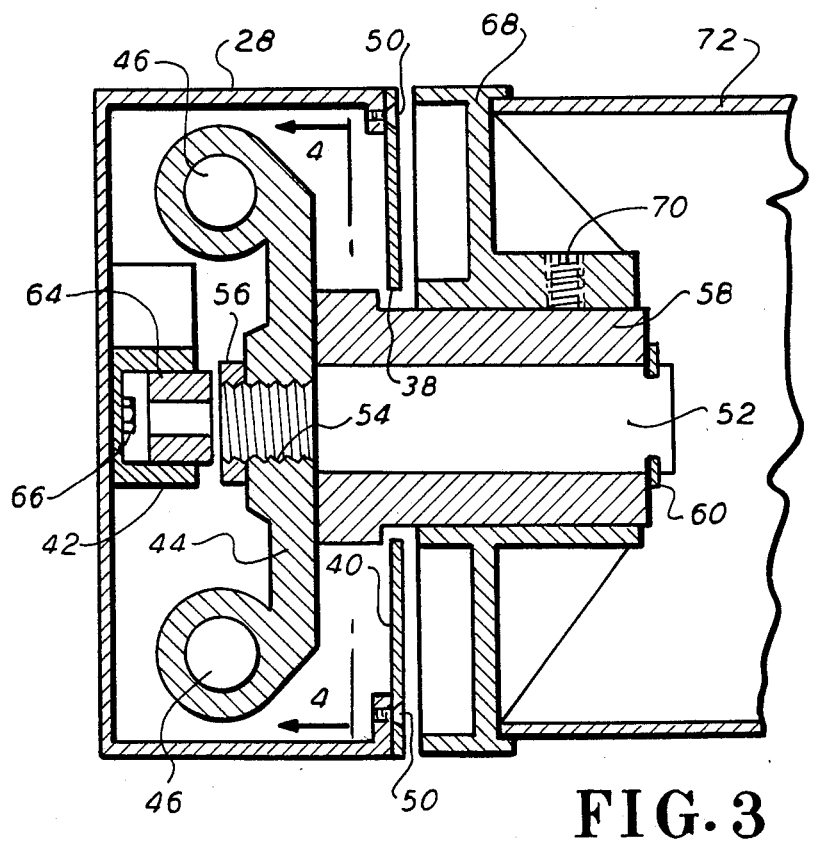
FIG. 3 is a side cross-sectional view of the mounting means of FIG. 2.
Figure 4:
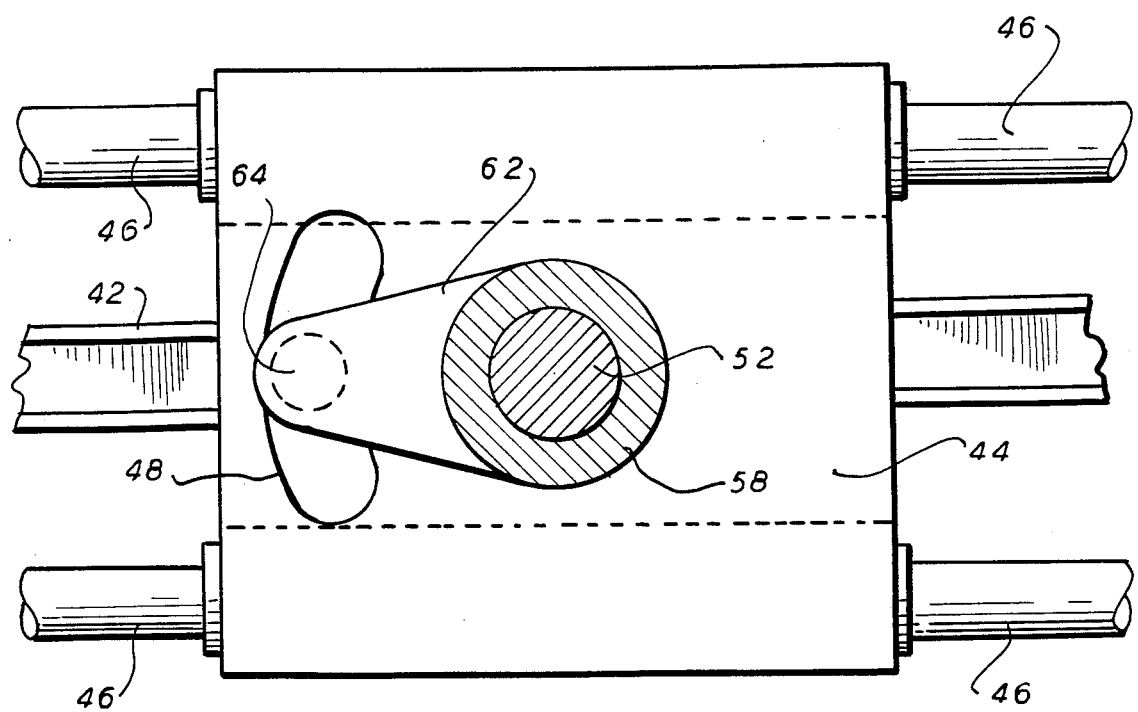
FIG. 4 is an enlarged front view of the mounting means of FIG. 2.

In FIG. 3 there is shown a side cross sectional view and in FIG. 4 a front sectional view of the heater traverse mechanism taken along the line 4—4 of FIG. 3.

As can be seen in FIGS. 3 and 4, the carriage 44 rides along the pair of rods 46. In the preferred form, rods 46 are steel rods and linear bearings are utilized so that carriage 44 rides smoothly and easily along the rods 46, however, lubricated sleeve bearings may also be utilized. The rods 46 as well as the carriage 44 are contained within upper cross member 28 having front cover 40 secured thereto by means such as screws 50. As also may be noted in FIG. 3, elongated opening 38 is formed in front cover 40.

A carriage stud 52 depends outwardly from carriage 44 and is firmly affixed to carriage 44 by screw threads 54 that fit within corresponding threads formed in carriage 44 and a jam nut 56 is screwed on to the end of carriage stud 52 to insure that carriage stud 52 is firmly and immovably affixed to the carriage 44.

A support post 58 is rotatably mounted on carriage stud 52 having one end thereof abutting against carriage 44 and the other end held in position by E-clip 60.

As may be more clearly seen in FIG. 4, support post 58 includes an eccentric 62 having a cam follower 64 that extends outwardly from the eccentric 62 through opening 48 in carriage 44 and fits within the inclined track 42 (FIG. 3).

Therefore, as the carriage 44 moves along the horizontal rods 46, cam follower 64 moves within the inclined track 42 and, since that inclined track 42 is affixed to the rear of the upper cross member 28 by means such as screws 66 at an angle to the horizontal, the support post 58 rotates about carriage stud 52.

Affixed to support post 58 is the heater housing end cap 68 by means such as a set screw 70. As a further part of heater 36, heater housing 72 extends outwardly from heater housing end cap 68 and which contains the focused heater itself (not shown). As noted, the actual heater element may be a Calrod heater having a reflector that focuses the heat onto a fixed focus on the infant. Alternatively, the heater element may be a corrugated foil type heater or one of several other types that preferably are linear radiant heaters, that is, the heater itself is along a linear length such that a rectangular footprint is directed upon the infant.

Figure 5:
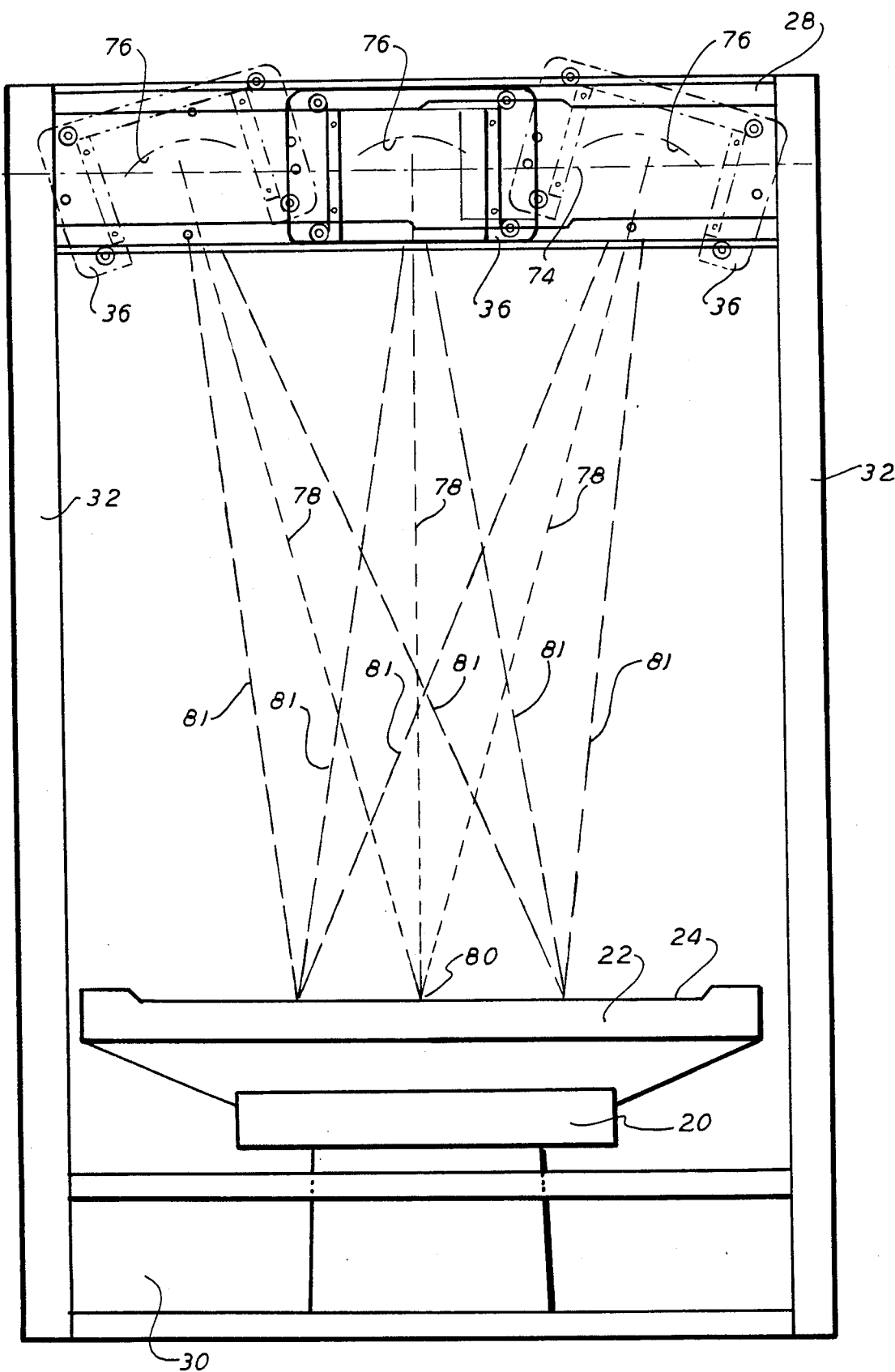
FIG. 5 is a front schematic view showing the heater mechanism of the preferred embodiment in various positions.

Turning now to FIG. 5, the focus of the heater 36 may be seen as the heater 36 is traversed along its locus of movement. In the FIG. 5 embodiment, the heater 36 moves along center line 74 generally horizontally in a plane parallel to the plane of the planar upper surface 24 of the infant bed 22. A reflector 76 (shown schematically) focuses the heater 36 to a fixed focus along the dotted lines 78 to a line 80 that forms a footprint generally directing the heat on the infant positioned atop infant bed 22. As further noted, the footprint width may generally be within the lines 81. The actual footprint itself is rectangular encompassing the entire infant. As the different positions of heater 36 are shown in FIG. 5, the heater 36 rotates by the traverse mechanism described with respect to FIGS. 2-4 and retains the focus of heater 36 along the same fixed center line 80. Thus heater 36 may be manually moved along a fixed locus, but the heat is maintained focused on the infant.

Figure 6:
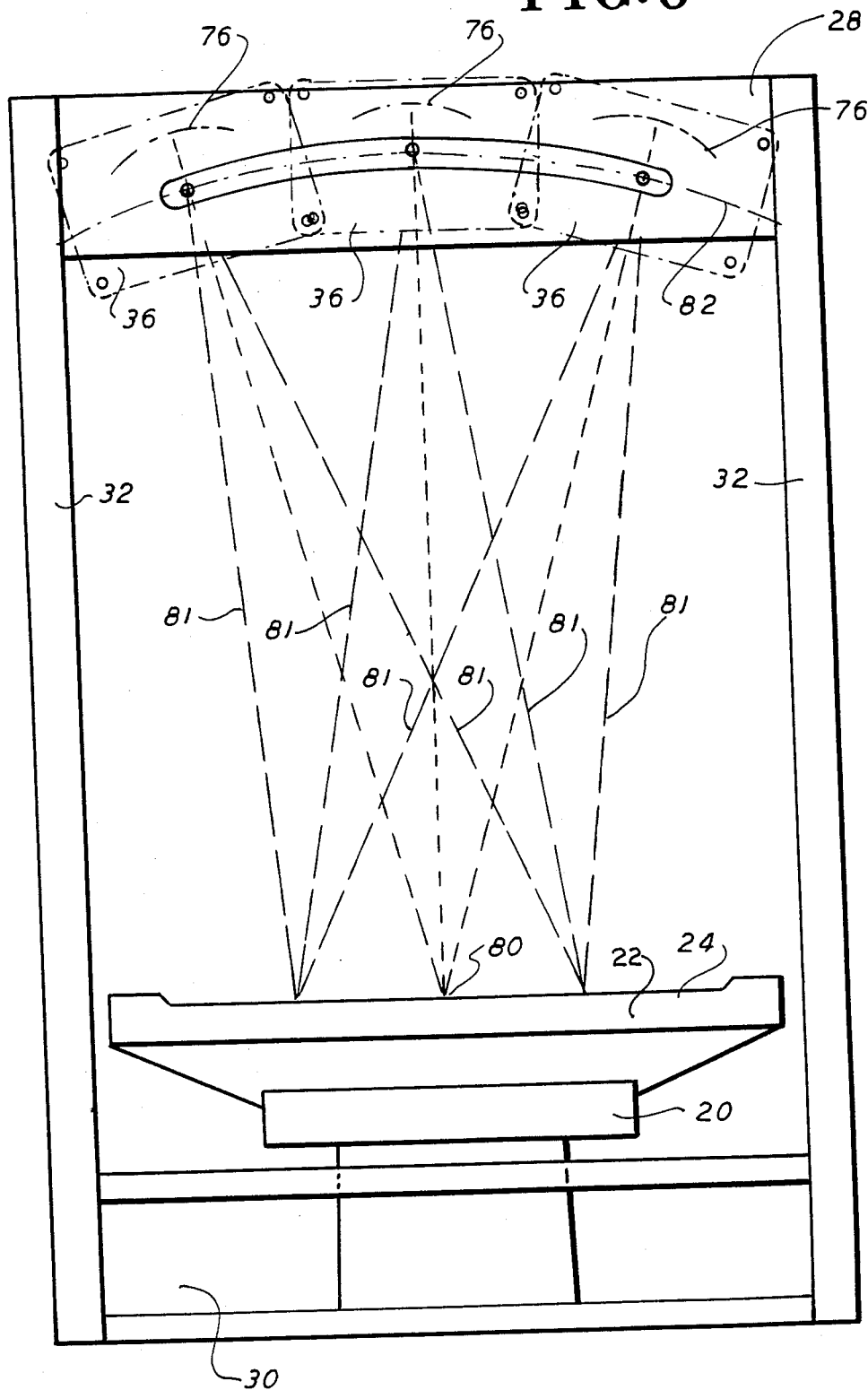
FIG. 6 is a front schematic view of an alternate embodiment of a heater traverse mechanism within the scope of the present invention showing the heater in various positions.

In FIG. 6, there is shown a schematic view of an alternate embodiment, that is, where the heater 36 moves along an arcuate center line 82 of a known radius and having, as its center point, the fixed center line 80 on the upper surface 24 of infant bed 22, thus, again, heater 36 may be manually moved along a locus to various positions, yet the focus of the heater 36 remains at the desired footprint directing the optimum heat on the infant.

While the invention has been disclosed and described with reference to a single embodiment, it will be apparent that variations and modifications may be made therein, and it is therefore intended in the following claims to cover each such variation and modification as falls within the true spirit and scope of the invention.

We claim:

1. An infant care unit comprising:
   a standing frame member;
   a generally planar infant bed affixed to said standing frame member and adapted to underlie an infant;
   a heater mounted to said standing frame member above said infant bed and focused to direct heat on or about an infant positioned on said infant bed;
   mounting means for mounting said heater to said frame member to constrain said heater to be manually moved along a locus while maintaining the focus of said heater on the same location on said infant bed.

2. An infant care unit as defined in claim 1 wherein said locus along which said heater is moveable is a radial arc having, as the centerpoint, the position of the infant.

3. An infant care unit as defined in claim 1 wherein said locus along which said heater is moveable is in a plane generally parallel to the plane of said infant bed and said heater rotates to maintain the focus on or about the infant.

4. An infant care unit as defined in claim 3 wherein said heater is a linear radiant heater providing a rectangular footprint on the infant.

5. An infant care unit comprising:
   a standing frame member;
   a generally planar infant bed suspended from said frame member and adapted to underlie an infant;
   a heater mounted to said frame member above said infant bed and adapted to be focused to direct heat on or about an infant positioned on said infant bed;
   mounting means for said heater to allow said heater to be moved laterally across said infant bed in a plane generally parallel with the plane of said planar infant bed; and
   said mounting means further adapted to rotate said heater as said heater moves laterally across said infant bed to retain the focus of said heater on the same general location on said infant bed.

6. An infant care unit as defined in claim 5 wherein said mounting means comprises a bearing means supported by said frame member on which said heater is mounted, and said mounting means causes said heater to rotate as said heater is moved thereacross.

7. An infant care unit as defined in claim 6 wherein said mounting means further comprises an inclined track mounted to said frame, and said heater includes an elongated arm depending outwardly therefrom and having a cam at the outward end thereof, said cam being adapted to fit within said inclined track to rotate said heater as said heater moves along said bearing means.

8. An infant care unit as defined in claim 7 wherein said heater comprises a linear radiant heater providing a rectangular footprint on said infant.

9. An infant care unit as defined in claim 7 wherein said bearing means comprises a linear bearing.

* * * * *